(12) United States Patent
Guo et al.

(10) Patent No.: US 9,194,010 B2
(45) Date of Patent: Nov. 24, 2015

(54) PHYTASE HAVING IMPROVED ENZYMATIC ACTIVITY

(71) Applicant: Dongguan APAC Biotechnology CO., Ltd., DongGuan (CN)

(72) Inventors: Rey-Ting Guo, Taipei (TW); Tzu-Hui Wu, Taipei (TW); Ya-Shan Cheng, Taipei (TW); Jian-Wen Huang, Taipei (TW); Hui-Lin Lai, Taipei (TW); Cheng-Yen Lin, Taipei (TW); Ting-Yung Huang, Taipei (TW)

(73) Assignee: DONGGUAN APAC BIOTECHNOLOGY CO., LTD., DongGuan (CN)

( * ) Notice: Subject to any disclaimer, the term of this patent is extended or adjusted under 35 U.S.C. 154(b) by 16 days.

(21) Appl. No.: 14/337,884

(22) Filed: Jul. 22, 2014

(65) Prior Publication Data

US 2015/0031110 A1 Jan. 29, 2015

(30) Foreign Application Priority Data

Jul. 24, 2013 (TW) .............................. 102126555 A

(51) Int. Cl.
*C12N 9/16* (2006.01)

(52) U.S. Cl.
CPC ........... *C12Y 301/03008* (2013.01); *C12N 9/16* (2013.01); *C12Y 301/03026* (2013.01)

(58) Field of Classification Search
None
See application file for complete search history.

(56) References Cited

PUBLICATIONS

Wu et al. J Biotechnol. Apr. 10, 2014;175:1-6.*

* cited by examiner

*Primary Examiner* — Christian Fronda
(74) *Attorney, Agent, or Firm* — Kirton McConkie; Evan R. Witt

(57) ABSTRACT

A phytase having improved enzymatic activity is disclosed. The phytase has a modified amino acid sequence of SEQ ID NO: 2, wherein the modification is a substitution of Valine at position 90 with Threonine. Alternatively, the phytase has a modified amino acid sequence of SEQ ID NO: 6, wherein the modification is a substitution of Asparagine at position 204 with Alanine or a substitution of Serine at position 206 with Alanine.

9 Claims, 9 Drawing Sheets

```
atgcagagtgagccggagctgaagctggaaagtgtggtgattgtcagtcgtcatggtgtgcgtgctccaaccaaggccacgcaactgatg
 M  Q  S  E  P  E  L  K  L  E  S  V  V  I  V  S  R  H  G  V  R  A  P  T  K  A  T  Q  L  M caggatgtcaccccagacgcatggccaacctggccggtaaaactgggttggctgacaccgcggtggtgagctaatcgcctatctcgga
 Q  D  V  T  P  D  A  W  P  T  W  P  V  K  L  G  W  L  T  P  R  G  G  E  L  I  A  Y  L  G cattaccaacgccagcgtctggcagccgacggattgctggcgaaaaagggctgcccgctgtctggtcaggtcgcgattattgctgatgtc
 H  Y  Q  R  Q  R  L  A  A  D  G  L  L  A  K  K  G  C  P  L  S  G  Q  V  A  I  I  A  D  V gacgagcgtacccgtaaaacaggcgaagccttcgccgccgggctggcacctgactgtgcaataaccgtacatacccaggcagatacgtcc
 D  E  R  T  R  K  T  G  E  A  F  A  A  G  L  A  P  D  C  A  I  T  V  H  T  Q  A  D  T  S agtcccgatccgttatttaatcctctaaaaactggcgtttgccaactggataacgcgaacgtgactgacgcgatcctcagcagggcagga
 S  P  D  P  L  F  N  P  L  K  T  G  V  C  Q  L  D  N  A  N  V  T  D  A  I  L  S  R  A  G gggtcaattgctgactttaccgggcatcggcaaacgcgtttcgcgaactggaacgggtgcttaattttccgcaatcaaacttgtgcctt
 G  S  I  A  D  F  T  G  H  R  Q  T  A  F  R  E  L  E  R  V  L  N  F  P  Q  S  N  L  C  L aaacgtgagaaacaggacgaaagctgttcattaacgcaggcattaccatcggaactcaaggtgagcgccgacaatgtctcattaaccggt
 K  R  E  K  Q  D  E  S  C  S  L  T  Q  A  L  P  S  E  L  K  V  S  A  D  N  V  S  L  T  G gcggtaagcctcgcatcaatgctgacggagatatttctcctgcaacaagcacagggaatgccggagccggggtggggaaggatcaccgat
 A  V  S  L  A  S  M  L  T  E  I  F  L  L  Q  Q  A  Q  G  M  P  E  P  G  W  G  R  I  T  D tcacaccagtggaacaccttgctaagtttgcataacgcgcaattttatttgttacaacgcacgcagaggttgcccgcagccgcgccacc
 S  H  Q  W  N  T  L  L  S  L  H  N  A  Q  F  Y  L  L  Q  R  T  P  E  V  A  R  S  R  A  T ccgttattagatttgatcaagacagcgttgacgccccatccaccgcaaaaacaggcgtatggtgtgacattacccacttcagtgctgttt
 P  L  L  D  L  I  K  T  A  L  T  P  H  P  P  Q  K  Q  A  Y  G  V  T  L  P  T  S  V  L  F atcgccggacacgatactaatctggcaaatctcggcggcgcactggagctcaactggacgcttcccggtcagccggataacacgccgcca
 I  A  G  H  D  T  N  L  A  N  L  G  G  A  L  E  L  N  W  T  L  P  G  Q  P  D  N  T  P  P ggtggtgaactggtgtttgaacgctggcgtcggctaagcgataacagccagtggattcaggtttcgctggtcttccagactttacagcag
 G  G  E  L  V  F  E  R  W  R  R  L  S  D  N  S  Q  W  I  Q  V  S  L  V  F  Q  T  L  Q  Q atgcgtgataaaacgccgctgtcattaaatacgccgcccggagaggtgaaactgaccctggcaggatgtgaagagcgaaatgcgcagggc
 M  R  D  K  T  P  L  S  L  N  T  P  P  G  E  V  K  L  T  L  A  G  C  E  E  R  N  A  Q  G atgtgttcgttggcaggttttacgcaaatcgtgaatgaagcacgcataccggcgtgcagtttgtaa -SEQ ID NO: 1
 M  C  S  L  A  G  F  T  Q  I  V  N  E  A  R  I  P  A  C  S  L  *  -SEQ ID NO: 2
```

FIG. 2

| Mutant | Primer sequence (5' --> 3') |
|--------|------------------------------|
| Ec-V90T | GCGATTATTGCTGAT<u>ACC</u>GACGAGCGTACCCGT |
| r-N204A | AAGGTCTCCGCCGAC<u>GCT</u>GTCTCTTTGACCGGT |
| r-S206A | TCCGCCGACAACGTC<u>GCT</u>TTGACCGGTGCTGTC |

FIG. 3

```
atgcagagtgagccggagctgaagctggaaagtgtggtgattgtcagtcgtcatggtgtgcgtgctccaaccaaggccacgcaactgatg
 M  Q  S  E  P  E  L  K  L  E  S  V  V  I  V  S  R  H  G  V  R  A  P  T  K  A  T  Q  L  M caggatgtcaccccagacgcatggccaacctggccggtaaaactgggttggctgacaccgcggtggtgagctaatcgcctatctcgga
 Q  D  V  T  P  D  A  W  P  T  W  P  V  K  L  G  W  L  T  P  R  G  G  E  L  I  A  Y  L  G cattaccaacgccagcgtctggcagccgacggattgctggcgaaaaagggctgcccgctgtctggtcaggtcgcgattattgctgatacc
 H  Y  Q  R  Q  R  L  A  A  D  G  L  L  A  K  K  G  C  P  L  S  G  Q  V  A  I  I  A  D  T gacgagcgtacccgtaaaacaggcgaagccttcgccgccgggctggcacctgactgtgcaataaccgtacataccccaggcagatacgtcc
 D  E  R  T  R  K  T  G  E  A  F  A  A  G  L  A  P  D  C  A  I  T  V  H  T  Q  A  D  T  S agtcccgatccgttatttaatcctctaaaaactggcgtttgccaactggataacgcgaacgtgactgacgcgatcctcagcagggcagga
 S  P  D  P  L  F  N  P  L  K  T  G  V  C  Q  L  D  N  A  N  V  T  D  A  I  L  S  R  A  G gggtcaattgctgactttaccgggcatcggcaaacggcgtttcgcgaactggaacggtgcttaattttccgcaatcaaacttgtgcctt
 G  S  I  A  D  F  T  G  H  R  Q  T  A  F  R  E  L  E  R  V  L  N  F  P  Q  S  N  L  C  L aaacgtgagaaacaggacgaaagctgttcattaacgcaggcattaccatcggaactcaaggtgagcgccgacaatgtctcattaaccggt
 K  R  E  K  Q  D  E  S  C  S  L  T  Q  A  L  P  S  E  L  K  V  S  A  D  N  V  S  L  T  G gcggtaagcctcgcatcaatgctgacggagatatttctcctgcaacaagcacagggaatgccggagccggggtggggaaggatcaccgat
 A  V  S  L  A  S  M  L  T  E  I  F  L  L  Q  Q  A  Q  G  M  P  E  P  G  W  G  R  I  T  D tcacaccagtggaacaccttgctaagtttgcataacgcgcaatttatttgttacaacgcacgccagaggttgcccgcagccgcgccacc
 S  H  Q  W  N  T  L  L  S  L  H  N  A  Q  F  Y  L  L  Q  R  T  P  E  V  A  R  S  R  A  T ccgttattagatttgatcaagacagcgttgacgccccatccaccgcaaaaacaggcgtatggtgtgacattacccacttcagtgctgttt
 P  L  L  D  L  I  K  T  A  L  T  P  H  P  P  Q  K  Q  A  Y  G  V  T  L  P  T  S  V  L  F atcgccggacacgatactaatctggcaaatctcggcggcgcactggagctcaactggacgcttcccggtcagccggataacacgccgcca
 I  A  G  H  D  T  N  L  A  N  L  G  G  A  L  E  L  N  W  T  L  P  G  Q  P  D  N  T  P  P ggtggtgaactggtgtttgaacgctggcgtcggctaagcgataacagccagtggattcaggtttcgctggtcttccagactttacagcag
 G  G  E  L  V  F  E  R  W  R  R  L  S  D  N  S  Q  W  I  Q  V  S  L  V  F  Q  T  L  Q  Q atgcgtgataaaacgccgctgtcattaaatacgccgccggagaggtgaaactgaccctggcaggatgtgaagagcgaaatgcgcagggc
 M  R  D  K  T  P  L  S  L  N  T  P  P  G  E  V  K  L  T  L  A  G  C  E  E  R  N  A  Q  G atgtgttcgttggcaggttttacgcaaatcgtgaatgaagcacgcataccggcgtgcagtttgtaa   -SEQ ID NO: 3
 M  C  S  L  A  G  F  T  Q  I  V  N  E  A  R  I  P  A  C  S  L  *     -SEQ ID NO: 4
```

FIG. 4

```
cagagtgagcctgagttgaaactggaatccgttgtcatcgtctctagacatggtgttagagcaccaaccaaggccacccaacttatgcaa
 Q  S  E  P  E  L  K  L  E  S  V  V  I  V  S  R  H  G  V  R  A  P  T  K  A  T  Q  L  M  Q gatgtcaccccagacgcttggccaacctggccagtcaagctgggttggttgacacctagaggtggtgagctcattgcttacttgggtcac
 D  V  T  P  D  A  W  P  T  W  P  V  K  L  G  W  L  T  P  R  G  G  E  L  I  A  Y  L  G  H taccaaagacagcgtcttgttgccgacggattgttggccaagaagggttgtccacaatctggtcaagtagctattattgctgacgtcgac
 Y  Q  R  Q  R  L  V  A  D  G  L  L  A  K  K  G  C  P  Q  S  G  Q  V  A  I  I  A  D  V  D gaaagaacccgtaagacaggtgaagccttcgccgccggtcttgctcctgactgtgccattaccgttcacacccaagttgacacttcttct
 E  R  T  R  K  T  G  E  A  F  A  A  G  L  A  P  D  C  A  I  T  V  H  T  Q  V  D  T  S  S ccagatccattgttcaaccctttgaagactggtgtttgccaattggacaacgctaacgttactgacgctatcttgtccagagctggagga
 P  D  P  L  F  N  P  L  K  T  G  V  C  Q  L  D  N  A  N  V  T  D  A  I  L  S  R  A  G  G tccattgctgacttcaccggtcacagacagactgccttcagagagttggaaagagttcttaacttcccacaatccaacttgtgccttaag
 S  I  A  D  F  T  G  H  R  Q  T  A  F  R  E  L  E  R  V  L  N  F  P  Q  S  N  L  C  L  K cgtgagaagcaagacgaatcctgttccttgactcaagcattaccatctgagttgaaggtctccgccgacaacgtctctttgaccggtgct
 R  E  K  Q  D  E  S  C  S  L  T  Q  A  L  P  S  E  L  K  V  S  A  D  N  V  S  L  T  G  A gtcagcttggcttccatgttgactgaaatctttcttctgcaacaagctcaaggtatgcctgagccaggttggggtagaatcaccgactct
 V  S  L  A  S  M  L  T  E  I  F  L  L  Q  Q  A  Q  G  M  P  E  P  G  W  G  R  I  T  D  S caccaatggaacaccttgttgtccttgcacaacgctcaattctacttgctgcagagaactccagaggttgctagatccagagctaccccca
 H  Q  W  N  T  L  L  S  L  H  N  A  Q  F  Y  L  L  Q  R  T  P  E  V  A  R  S  R  A  T  P ttgttggacttgatcaagactgcttttgactcctcacccacctcaaaagcaagcctacggtgttaccttgcccacttctgtcttgttcatt
 L  L  D  L  I  K  T  A  L  T  P  H  P  P  Q  K  Q  A  Y  G  V  T  L  P  T  S  V  L  F  I gccggtcacgatactaacttggcaaatctcggcggtgctttggagttgaactggactcttcctggtcaacctgataacactccaccaggt
 A  G  H  D  T  N  L  A  N  L  G  G  A  L  E  L  N  W  T  L  P  G  Q  P  D  N  T  P  P  G ggtgagctcgttttcgaaagatggcgtagactatctgataactctcaatggattcaggtttcgttggtcttccaaactttgcagcagatg
 G  E  L  V  F  E  R  W  R  R  L  S  D  N  S  Q  W  I  Q  V  S  L  V  F  Q  T  L  Q  Q  M agagacaagactccactgtctttgaacacgcctccaggagaagtcaaattgaccttggctggatgtgaagagagaaatgctcagggtatg
 R  D  K  T  P  L  S  L  N  T  P  P  G  E  V  K  L  T  L  A  G  C  E  E  R  N  A  Q  G  M tgttccttggctggtttcactcaaatcgttaacgaagctagaatcccagcttgttccttgtag   -SEQ ID NO: 5
 C  S  L  A  G  F  T  Q  I  V  N  E  A  R  I  P  A  C  S  L  *     -SEQ ID NO: 6
```

FIG. 5

```
cagagtgagcctgagttgaaactggaatccgttgtcatcgtctctagacatggtgttagagcaccaaccaaggccacccaacttatgcaa
 Q  S  E  P  E  L  K  L  E  S  V  V  I  V  S  R  H  G  V  R  A  P  T  K  A  T  Q  L  M  Q gatgtcaccccagacgcttggccaacctggccagtcaagctgggttggttgacacctagaggtggtgagctcattgcttacttgggtcac
 D  V  T  P  D  A  W  P  T  W  P  V  K  L  G  W  L  T  P  R  G  G  E  L  I  A  Y  L  G  H taccaaagacagcgtcttgttgccgacggattgttggccaagaaggggtgtccacaatctggtcaagtagctattattgctgacgtcgac
 Y  Q  R  Q  R  L  V  A  D  G  L  L  A  K  K  G  C  P  Q  S  G  Q  V  A  I  I  A  D  V  D gaaagaacccgtaagacaggtgaagccttcgccgccggtcttgctcctgactgtgccattaccgttcacacccaagttgacacttcttct
 E  R  T  R  K  T  G  E  A  F  A  A  G  L  A  P  D  C  A  I  T  V  H  T  Q  V  D  T  S  S ccagatccattgttcaacccttttgaagactggtgtttgccaattggacaacgctaacgttactgacgctatcttgtccagagctggagga
 P  D  P  L  F  N  P  L  K  T  G  V  C  Q  L  D  N  A  N  V  T  D  A  I  L  S  R  A  G  G tccattgctgacttcaccggtcacagacagactgccttcagagagttggaaagagttcttaacttcccacaatccaacttgtgccttaag
 S  I  A  D  F  T  G  H  R  Q  T  A  F  R  E  L  E  R  V  L  N  F  P  Q  S  N  L  C  L  K cgtgagaagcaagacgaatcctgttccttgactcaagcattaccatctgagttgaaggtctccgcgac gct gtctctttgaccggtgct
 R  E  K  Q  D  E  S  C  S  L  T  Q  A  L  P  S  E  L  K  V  S  A  D [A] V  S  L  T  G  A gtcagcttggcttccatgttgactgaaatctttcttctgcaacaagctcaaggtatgcctgagccaggttggggtagaatcaccgactct
 V  S  L  A  S  M  L  T  E  I  F  L  L  Q  Q  A  Q  G  M  P  E  P  G  W  G  R  I  T  D  S caccaatggaacaccttgttgtccttgcacaacgctcaattctacttgctgcagagaactccagaggttgctagatccagagccacccca
 H  Q  W  N  T  L  L  S  L  H  N  A  Q  F  Y  L  L  Q  R  T  P  E  V  A  R  S  R  A  T  P ttgttggacttgatcaagactgctttgactcctcacccacctcaaaagcaagcctacggtgttacccttgccacttctgtcttgttcatt
 L  L  D  L  I  K  T  A  L  T  P  H  P  P  Q  K  Q  A  Y  G  V  T  L  P  T  S  V  L  F  I gccggtcacgatactaacttggcaaatctcggcggtgctttggagttgaactggactcttcctggtcaacctgataacactccaccaggt
 A  G  H  D  T  N  L  A  N  L  G  G  A  L  E  L  N  W  T  L  P  G  Q  P  D  N  T  P  P  G ggtgagctcgttttcgaaagatggcgtagactatctgataactctcaatggattcaggtttcgttggtcttccaaactttgcagcagatg
 G  E  L  V  F  E  R  W  R  R  L  S  D  N  S  Q  W  I  Q  V  S  L  V  F  Q  T  L  Q  Q  M agagacaagactccactgtctttgaacacgcctccaggagaagtcaaattgaccttggctggatgtgaagagagaaatgctcagggtatg
 R  D  K  T  P  L  S  L  N  T  P  G  E  V  K  L  T  L  A  G  C  E  E  R  N  A  Q  G  M tgttccttggctggtttcactcaaatcgttaacgaagctagaatcccagcttgttccttgtag         -SEQ ID NO: 7
 C  S  L  A  G  F  T  Q  I  V  N  E  A  R  I  P  A  C  S  L  *          -SEQ ID NO: 8
```

FIG. 6

```
cagagtgagcctgagttgaaactggaatccgttgtcatcgtctctagacatggtgttagagcaccaaccaaggccacccaacttatgcaa
 Q  S  E  P  E  L  K  L  E  S  V  V  I  V  S  R  H  G  V  R  A  P  T  K  A  T  Q  L  M  Q gatgtcaccccagacgcttggccaacctggccagtcaagctgggttggttgacacctagaggtggtgagctcattgcttacttgggtcac
 D  V  T  P  D  A  W  P  T  W  P  V  K  L  G  W  L  T  P  R  G  G  E  L  I  A  Y  L  G  H taccaaagacagcgtcttgttgccgacggattgttggccaagaagggttgtccacaatctggtcaagtagctattattgctgacgtcgac
 Y  Q  R  Q  R  L  V  A  D  G  L  L  A  K  K  G  C  P  Q  S  G  Q  V  A  I  I  A  D  V  D gaaagaacccgtaagacaggtgaagccttcgccgccggtcttgctcctgactgtgccattaccgttcacacccaagttgacacttcttct
 E  R  T  R  K  T  G  E  A  F  A  A  G  L  A  P  D  C  A  I  T  V  H  T  Q  V  D  T  S  S ccagatccattgttcaacccttttgaagactggtgtttgccaattggacaacgctaacgttactgacgctatcttgtccagagctggagga
 P  D  P  L  F  N  P  L  K  T  G  V  C  Q  L  D  N  A  N  V  T  D  A  I  L  S  R  A  G  G tccattgctgacttcaccggtcacagacagactgccttcagagagttggaaagagttcttaacttcccacaatccaacttgtgccttaag
 S  I  A  D  F  T  G  H  R  Q  T  A  F  R  E  L  E  R  V  L  N  F  P  Q  S  N  L  C  L  K cgtgagaagcaagacgaatcctgttccttgactcaagcattaccatctgagttgaaggtctccgccgacaacgtcgctttgaccggtgct
 R  E  K  Q  D  E  S  C  S  L  T  Q  A  L  P  S  E  L  K  V  S  A  D  N  V [A] L  T  G  A gtcagcttggcttccatgttgactgaaatctttcttctgcaacaagctcaaggtatgcctgagccaggttggggtagaatcaccgactct
 V  S  L  A  S  M  L  T  E  I  F  L  L  Q  Q  A  Q  G  M  P  E  P  G  W  G  R  I  T  D  S caccaatggaacaccttgttgtccttgcacaacgctcaattctacttgctgcagagaactccagaggttgctagatccagagccacccca
 H  Q  W  N  T  L  L  S  L  H  N  A  Q  F  Y  L  L  Q  R  T  P  E  V  A  R  S  R  A  T  P ttgttggacttgatcaagactgcttttgactcctcacccacctcaaaagcaagcctacggtgttaccttgcccacttctgtcttgttcatt
 L  L  D  L  I  K  T  A  L  T  P  H  P  P  Q  K  Q  A  Y  G  V  T  L  P  T  S  V  L  F  I gccggtcacgatactaacttggcaaatctcggcggtgctttggagttgaactggactcttcctggtcaacctgataacactccaccaggt
 A  G  H  D  T  N  L  A  N  L  G  G  A  L  E  L  N  W  T  L  P  G  Q  P  D  N  T  P  P  G ggtgagctcgttttcgaaagatggcgtagactatctgataactctcaatggattcaggtttcgttggtcttccaaactttgcagcagatg
 G  E  L  V  F  E  R  W  R  R  L  S  D  N  S  Q  W  I  Q  V  S  L  V  F  Q  T  L  Q  Q  M agagacaagactccactgtctttgaacacgcctccaggagaagtcaaattgaccttggctggatgtgaagagagaaatgctcagggtatg
 R  D  K  T  P  L  S  L  N  T  P  P  G  E  V  K  L  T  L  A  G  C  E  E  R  N  A  Q  G  M tgttccttggctggtttcactcaaatcgttaacgaagctagaatcccagcttgttccttgtag   -SEQ ID NO: 9
 C  S  L  A  G  F  T  Q  I  V  N  E  A  R  I  P  A  C  S  L  *     -SEQ ID NO: 10
```

FIG. 7

SEQUENCE LISTING

<160> NUMBER OF SEQ ID NOS: 10

<210> SEQ ID NO 1
<211> LENGTH: 1236
<212> TYPE: DNA
<213> ORGANISM: Escherichia coli

<400> SEQUENCE: 1

```
atgcagagtg agccggagct gaagctggaa agtgtggtga ttgtcagtcg tcatggtgtg      60
cgtgctccaa ccaaggccac gcaactgatg caggatgtca ccccagacgc atggccaacc     120
tggccggtaa aactgggttg gctgacaccg cgcggtggtg agctaatcgc ctatctcgga     180
cattaccaac gccagcgtct ggcagccgac ggattgctgg cgaaaaaggg ctgcccgctg     240
tctggtcagg tcgcgattat tgctgatgtc gacgagcgta cccgtaaaac aggcgaagcc     300
ttcgccgccg ggctggcacc tgactgtgca ataaccgtac atacccaggc agatacgtcc     360
agtcccgatc cgttatttaa tcctctaaaa actggcgttt gccaactgga taacgcgaac     420
```

```
gtgactgacg cgatcctcag cagggcagga gggtcaattg ctgactttac cgggcatcgg    480
caaacggcgt ttcgcgaact ggaacgggtg cttaattttc cgcaatcaaa cttgtgcctt    540
aaacgtgaga acaggacga aagctgttca ttaacgcagg cattaccatc ggaactcaag    600
gtgagcgccg acaatgtctc attaaccggt gcggtaagcc tcgcatcaat gctgacggag    660
atatttctcc tgcaacaagc acagggaatg ccggagccgg ggtggggaag atcaccgat    720 tcacaccagt ggaacacctt gctaagtttg cataacgcgc aattttattt gttacaacgc    780
acgccagagg ttgcccgcag ccgcgccacc ccgttattag atttgatcaa gacagcgttg    840
acgccccatc caccgcaaaa acaggcgtat ggtgtgacat tacccacttc agtgctgttt    900
atcgccggac acgatactaa tctggcaaat ctcggcggcg cactggagct caactggacg    960
cttcccggtc agccggataa cacgccgcca ggtggtgaac tggtgtttga acgctggcgt   1020
cggctaagcg ataacagcca gtggattcag gtttcgctgg tcttccagac tttacagcag   1080
atgcgtgata aaacgccgct gtcattaaat acgccgcccg gagaggtgaa actgaccctg   1140
gcaggatgtg aagagcgaaa tgcgcagggc atgtgttcgt tggcaggttt tacgcaaatc   1200
gtgaatgaag cacgcatacc ggcgtgcagt ttgtaa                             1236
```

<210> SEQ ID NO 2
<211> LENGTH: 411
<212> TYPE: PRT
<213> ORGANISM: Escherichia coli

<400> SEQUENCE: 2

```
Met Gln Ser Glu Pro Glu Leu Lys Leu Glu Ser Val Val Ile Val Ser
 1               5                  10                  15

Arg His Gly Val Arg Ala Pro Thr Lys Ala Thr Gln Leu Met Gln Asp
             20                  25                  30

Val Thr Pro Asp Ala Trp Pro Thr Trp Pro Val Lys Leu Gly Trp Leu
         35                  40                  45

Thr Pro Arg Gly Gly Glu Leu Ile Ala Tyr Leu Gly His Tyr Gln Arg
     50                  55                  60

Gln Arg Leu Ala Ala Asp Gly Leu Leu Ala Lys Lys Gly Cys Pro Leu
 65                  70                  75                  80

Ser Gly Gln Val Ala Ile Ile Ala Asp Val Asp Glu Arg Thr Arg Lys
                 85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Ser Arg Ala Gly Gly Ser Ile Ala Asp Phe Thr Gly His Arg
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Val Ser Leu Ala Ser Met Leu Thr Glu Ile Phe Leu Leu
    210                 215                 220
```

```
Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Tyr
            245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
            275                 280                 285

Ala Tyr Gly Val Thr Leu Pro Thr Ser Val Leu Phe Ile Ala Gly His
        290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
            325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 3
<211> LENGTH: 1236
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 3
atgcagagtg agccggagct gaagctggaa agtgtggtga ttgtcagtcg tcatggtgtg    60
cgtgctccaa ccaaggccac gcaactgatg caggatgtca ccccagacgc atggccaacc   120
tggccggtaa aactgggttg gctgacaccg cgcggtggtg agctaatcgc ctatctcgga   180
cattaccaac gccagcgtct ggcagccgac ggattgctgg cgaaaaaggg ctgcccgctg   240
tctggtcagg tcgcgattat tgctgatacc gacgagcgta cccgtaaaac aggcgaagcc   300
ttcgccgccg gctggcacc tgactgtgca ataaccgtac atacccaggc agatacgtcc   360
agtcccgatc cgttatttaa tcctctaaaa actggcgttt gccaactgga taacgcgaac   420
gtgactgacg cgatcctcag cagggcagga gggtcaattg ctgactttac cgggcatcgg   480
caaacggcgt ttcgcgaact ggaacgggtg cttaattttc gcaatcaaa cttgtgcctt   540 aaacgtgaga acaggacga agctgttca ttaacgcagg cattaccatc ggaactcaag   600
gtgagcgccg acaatgtctc attaaccggt gcggtaagcc tcgcatcaat gctgacggag   660
atatttctcc tgcaacaagc acagggaatg ccggagccgg ggtggggaag gatcaccgat   720
tcacaccagt ggaacacctt gctaagtttg cataacgcg aatttattt gttacaacgc   780 acgccagagg ttgcccgcag ccgcgccacc ccgttattag atttgatcaa gacagcgttg   840
acgccccatc caccgcaaaa acaggcgtat ggtgtgacat acccacttc agtgctgttt   900 atcgccggac acgatactaa tctggcaaat ctcggcggcg cactggagct caactggacg   960
```

```
cttcccggtc agccggataa cacgccgcca ggtggtgaac tggtgtttga acgctggcgt    1020
cggctaagcg ataacagcca gtggattcag gtttcgctgg tcttccagac tttacagcag    1080
atgcgtgata aaacgccgct gtcattaaat acgccgcccg agaggtgaa actgaccctg     1140 gcaggatgtg aagagcgaaa tgcgcagggc atgtgttcgt tggcaggttt tacgcaaatc    1200
gtgaatgaag cacgcatacc ggcgtgcagt ttgtaa                              1236
```

<210> SEQ ID NO 4
<211> LENGTH: 411
<212> TYPE: PRT
<213> ORGANISM: Artificial Sequence
<220> FEATURE:
<223> OTHER INFORMATION: Sequence synthetically translated from SEQ ID NO: 3

<400> SEQUENCE: 4

```
Met Gln Ser Glu Pro Glu Leu Lys Leu Glu Ser Val Val Ile Val Ser
 1               5                  10                  15

Arg His Gly Val Arg Ala Pro Thr Lys Ala Thr Gln Leu Met Gln Asp
             20                  25                  30

Val Thr Pro Asp Ala Trp Pro Thr Trp Pro Val Lys Leu Gly Trp Leu
         35                  40                  45

Thr Pro Arg Gly Gly Glu Leu Ile Ala Tyr Leu Gly His Tyr Gln Arg
     50                  55                  60

Gln Arg Leu Ala Ala Asp Gly Leu Leu Ala Lys Lys Gly Cys Pro Leu
 65                  70                  75                  80

Ser Gly Gln Val Ala Ile Ile Ala Asp Thr Asp Glu Arg Thr Arg Lys
                 85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Ser Arg Ala Gly Gly Ser Ile Ala Asp Phe Thr Gly His Arg
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Tyr
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
```

```
              305                 310                 315                 320
Leu Pro Gly Gln Pro Asp Asn Thr Pro Pro Gly Gly Glu Leu Val Phe
                    325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Ser
                355                 360                 365

Leu Asn Thr Pro Pro Gly Glu Val Lys Leu Thr Leu Ala Gly Cys Glu
            370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 5
<211> LENGTH: 1233
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 5
cagagtgagc ctgagttgaa actggaatcc gttgtcatcg tctctagaca tggtgttaga      60
gcaccaacca aggccaccca acttatgcaa gatgtcaccc cagacgcttg gccaacctgg     120
ccagtcaagc tgggttggtt gacacctaga ggtggtgagc tcattgctta cttgggtcac     180
taccaaagac agcgtcttgt tgccgacgga ttgttggcca agaagggttg tccacaatct     240
ggtcaagtag ctattattgc tgacgtcgac gaaagaaccc gtaagacagg tgaagccttc     300
gccgccggtc ttgctcctga ctgtgccatt accgttcaca cccaagttga cacttcttct     360
ccagatccat tgttcaaccc tttgaagact ggtgtttgcc aattggacaa cgctaacgtt     420
actgacgcta tcttgtccag agctggagga tccattgctg acttcaccgg tcacagacag     480
actgccttca gagagttgga aagagttctt aacttcccac aatccaactt gtgccttaag     540
cgtgagaagc aagacgaatc ctgttccttg actcaagcat accatctga gttgaaggtc     600 tccgccgaca cgtctctttt gaccggtgct gtcagcttgg cttccatgtt gactgaaatc     660
tttcttctgc aacaagctca aggtatgcct gagccaggtt ggggtagaat caccgactct     720
caccaatgga cacccttgtt gtccttgcac aacgctcaat tctacttgct gcagagaact     780
ccagaggttg ctagatccag agccacccca ttgttggact tgatcaagac tgcttttgact     840 cctcacccac tcaaaagca agcctacggt gttaccttgc ccacttctgt cttgttcatt     900
gccggtcacg atactaactt ggcaaatctc ggcggtgctt tggagttgaa ctggactctt     960
cctggtcaac tgataacac tccaccaggt ggtgagctcg ttttcgaaag atggcgtaga    1020
ctatctgata ctctcaatg gattcaggtt cgttggtct tccaaacttt gcagcagatg    1080
agagacaaga ctccactgtc tttgaacacg cctccaggag aagtcaaatt gaccttggct    1140
ggatgtgaag agaaaatgc tcagggtatg tgttccttgg ctggtttcac tcaaatcgtt    1200
aacgaagcta gaatcccagc ttgttccttg tag                               1233

<210> SEQ ID NO 6
<211> LENGTH: 410
<212> TYPE: PRT
<213> ORGANISM: Artificial Sequence
<220> FEATURE:
```

<223> OTHER INFORMATION: Sequence synthetically translated from SEQ ID
      NO: 5

<400> SEQUENCE: 6

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Val Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400
```

Asn Glu Ala Arg Ile Pro Ala Cys Ser Leu
         405                 410

<210> SEQ ID NO 7
<211> LENGTH: 1233
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 7

```
cagagtgagc ctgagttgaa actggaatcc gttgtcatcg tctctagaca tggtgttaga      60
gcaccaacca aggccaccca acttatgcaa gatgtcaccc agacgcttg gccaacctgg      120
ccagtcaagc tggttggtt gacacctaga ggtggtgagc tcattgctta cttgggtcac     180
taccaaagac agcgtcttgt tgccgacgga ttgttggcca agaagggttg tccacaatct     240
ggtcaagtag ctattattgc tgacgtcgac gaaagaaccc gtaagacagg tgaagccttc     300
gccgccggtc ttgctcctga ctgtgccatt accgttcaca cccaagttga cacttcttct     360
ccagatccat tgttcaaccc tttgaagact ggtgtttgcc aattggacaa cgctaacgtt     420
actgacgcta tcttgtccag agctggagga tccattgctg acttcaccgg tcacagacag     480
actgccttca gagagttgga aagagttctt aacttcccac aatccaactt gtgccttaag     540
cgtgagaagc aagacgaatc tgttccttg actcaagcat accatctga gttgaaggtc     600
tccgccgacg ctgtctcttt gaccggtgct gtcagcttgg cttccatgtt gactgaaatc     660
tttcttctgc aacaagctca aggtatgcct gagccaggtt ggggtagaat caccgactct     720
caccaatgga acaccttgtt gtccttgcac aacgctcaat tctacttgct gcagagaact     780
ccagaggttg ctagatccag agccacccca ttgttggact tgatcaagac tgctttgact     840
cctcacccac tcaaaagca agcctacggt gttaccttgc ccacttctgt cttgttcatt     900
gccggtcacg atactaactt ggcaaatctc ggcggtgctt tggagttgaa ctggactctt     960
cctggtcaac tgataacac tccaccaggt ggtgagctcg ttttcgaaag atggcgtaga    1020
ctatctgata actctcaatg gattcaggtt tcgttggtct tccaaacttt gcagcagatg    1080
agagacaaga ctccactgtc tttgaacacg cctccaggag aagtcaaatt gaccttggct    1140
ggatgtgaag agagaaatgc tcagggtatg tgttccttgg ctggtttcac tcaaatcgtt    1200
aacgaagcta gaatcccagc ttgttccttg tag                                 1233
```

<210> SEQ ID NO 8
<211> LENGTH: 410
<212> TYPE: PRT
<213> ORGANISM: Artificial Sequence
<220> FEATURE:
<223> OTHER INFORMATION: Sequence synthetically translated from SEQ ID
      NO: 7

<400> SEQUENCE: 8

Gln Ser Glu Pro Glu Leu Lys Leu Glu Ser Val Val Ile Val Ser Arg
 1               5                  10                  15

His Gly Val Arg Ala Pro Thr Lys Ala Thr Gln Leu Met Gln Asp Val
             20                  25                  30

Thr Pro Asp Ala Trp Pro Thr Trp Pro Val Lys Leu Gly Trp Leu Thr
         35                  40                  45

Pro Arg Gly Gly Glu Leu Ile Ala Tyr Leu Gly His Tyr Gln Arg Gln
     50                  55                  60

```
Arg Leu Val Ala Asp Gly Leu Ala Lys Lys Gly Cys Pro Gln Ser
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
                100                 105                 110

His Thr Gln Val Asp Thr Ser Ser Pro Asp Pro Leu Phe Asn Pro Leu
                115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Ala Val Ser Leu Thr
                195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
                275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gly Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
                370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 9
<211> LENGTH: 1233
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 9
cagagtgagc tgagttgaa actggaatcc gttgtcatcg tctctagaca tggtgttaga      60
```

-continued

```
gcaccaacca aggccaccca acttatgcaa gatgtcaccc cagacgcttg gccaacctgg      120
ccagtcaagc tgggttggtt gacacctaga ggtggtgagc tcattgctta cttgggtcac      180
taccaaagac agcgtcttgt tgccgacgga ttgttggcca agaagggttg tccacaatct      240
ggtcaagtag ctattattgc tgacgtcgac gaaagaaccc gtaagacagg tgaagccttc      300
gccgccggtc ttgctcctga ctgtgccatt accgttcaca cccaagttga cacttcttct      360
ccagatccat tgttcaaccc tttgaagact ggtgtttgcc aattggacaa cgctaacgtt      420
actgacgcta tcttgtccag agctggagga tccattgctg acttcaccgg tcacagacag      480
actgccttca gagagttgga aagagttctt aacttcccac aatccaactt gtgccttaag      540
cgtgagaagc aagacgaatc ctgttccttg actcaagcat taccatctga gttgaaggtc      600
tccgccgaca acgtcgcttt gaccggtgct gtcagcttgg cttccatgtt gactgaaatc      660
tttcttctgc aacaagctca aggtatgcct gagccaggtt ggggtagaat caccgactct      720
caccaatgga cacccttgtt gtccttgcac aacgctcaat tctacttgct gcagagaact      780
ccagaggttg ctagatccag agccacccca ttgttggact tgatcaagac tgctttgact      840
cctcacccac ctcaaaagca agcctacggt gttaccttgc ccacttctgt cttgttcatt      900
gccggtcacg atactaactt ggcaaatctc ggcggtgctt tggagttgaa ctggactctt      960
cctggtcaac tgataacac tccaccaggt ggtgagctcg ttttcgaaag atggcgtaga     1020
ctatctgata actctcaatg gattcaggtt tcgttggtct tccaaacttt gcagcagatg     1080
agagacaaga ctccactgtc tttgaacacg cctccaggag aagtcaaatt gaccttggct     1140
ggatgtgaag agagaaatgc tcagggtatg tgttccttgg ctggtttcac tcaaatcgtt     1200
aacgaagcta gaatcccagc ttgttccttg tag                                  1233
```

```
<210> SEQ ID NO 10
<211> LENGTH: 410
<212> TYPE: PRT
<213> ORGANISM: Artificial Sequence
<220> FEATURE:
<223> OTHER INFORMATION: Sequence synthetically translated from SEQ ID
      NO: 9

<400> SEQUENCE: 10

Gln Ser Glu Pro Glu Leu Lys Leu Glu Ser Val Val Ile Val Ser Arg
 1               5                  10                  15

His Gly Val Arg Ala Pro Thr Lys Ala Thr Gln Leu Met Gln Asp Val
             20                  25                  30

Thr Pro Asp Ala Trp Pro Thr Trp Pro Val Lys Leu Gly Trp Leu Thr
         35                  40                  45

Pro Arg Gly Gly Glu Leu Ile Ala Tyr Leu Gly His Tyr Gln Arg Gln
     50                  55                  60

Arg Leu Val Ala Asp Gly Leu Leu Ala Lys Lys Gly Cys Pro Gln Ser
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
            100                 105                 110

His Thr Gln Val Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140
```

```
Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ala Leu Thr
            195                 200                 205

Gly Ala Val Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Gln Lys Gln Ala
            275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

PHYTASE HAVING IMPROVED ENZYMATIC ACTIVITY

FIELD OF THE INVENTION

The present invention relates to a phytase, and more particularly to a phytase having improved enzymatic activity.

BACKGROUND OF THE INVENTION

Phytic acid or phytate (myo-inositol hexakisphosphate) is the primary storage form of phosphorus in most plants and is abundant in seeds and legumes. However, the monogastric animals cannot utilize phosphorous from phytate due to the lack of necessary enzymes in digestive tract. Supplementation of inorganic phosphates was used to compensate the shortage in phosphorus ingestion but the excessive phosphorus in animal excretion has caused environmental pollution. In addition, the insoluble complexes formed by the highly negatively charged phytate with proteins and metal ions are major anti-nutritional factors. Phytase can hydrolyze phytate to lower inositol phosphates to release inorganic phosphate and thus has been widely applied in animal feeds to increase phosphorus availability and reduce phosphorus pollution. To date, phytase is estimated to account for 60% of feed enzyme products. Therefore, searching for phytases with higher specific activity and thermostability to lower the production cost and to survive the transient high-temperature step in pelleting procedure (80-85° C.) is of great interest to industries.

Classified by protein structure and catalytic property, there are four types of phytases including histidine acid phosphatases (HAPs), protein tyrosine phosphatase (PTP)-like phytases, purple acid phosphatases (PAPs) and β-propeller phytases (BPPs), with a majority of the characterized enzymes belonging to HAP. From previous studies, the crystal structures of all families except for PAP have been solved. Among the characterized phytases, *Escherichia coli* phytase (EcAppA), a member of the HAP family, has drawn much attention. First, EcAppA has high specific activity (up 56 to 2000 U/mg) under the favorable pH profile for feed additive. Second, large scale production of EcAppA in an industrial strain of *Pichia pastoris* has been successfully achieved by using fermentor for commercial applications. However, the need to enhance the enzymatic activity of EcAppA still remains.

Molecular engineering is a powerful approach to modify enzyme performances. Directed evolution involving random mutagenesis which builds a library provides a large pool of mutants for subsequent screening for useful mutants. But the efficiency is low and the procedure is laborious. A more ideal way is rational design, which is realized by the increasing information of protein structure and the development of powerful bioinformatics tools. Major obstacle in conducting a successful rational design is how to choose the useful residues or structural features.

In the present invention, site-directed mutagenesis of EcAppA is performed based on sequence comparison and structure analysis, so as to improve the industrial value of EcAppA.

SUMMARY OF THE INVENTION

An object of the present invention is to modify the phytase by means of sequence comparison, structural analysis and site-directed mutagenesis to efficiently increase the enzymatic activity, and improve its economic value of industrial application.

According to an aspect of the present invention, there is provided a phytase comprising a modified amino acid sequence of SEQ ID NO: 2, wherein the modification is a substitution of Valine at position 90 with Threonine.

In an embodiment, the amino acid sequence of SEQ ID NO: 2 is encoded by EcAppA gene isolated from *Escherichia coli*, and the phytase is a histidine acid phosphatase.

In an embodiment, the phytase has a full length amino acid sequence of SEQ ID NO: 4.

According to another aspect of the present invention, there is provided a phytase comprising a modified amino acid sequence of SEQ ID NO: 6, wherein the modification is a substitution of Asparagine at position 204 with Alanine or a substitution of Serine at position 206 with Alanine to remove a glycosylation position in an active site of the phytase.

In an embodiment, the amino acid sequence of SEQ ID NO: 6 is encoded by EcAppA gene isolated from *Escherichia coli* and optimized with codon usage, and the phytase is a histidine acid phosphatase.

In an embodiment, the phytase has a full length amino acid sequence of SEQ ID NO: 8.

In an embodiment, the phytase has a full length amino acid sequence of SEQ ID NO: 10.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 2 shows the gene sequence and the amino acid sequence of the wild-type EcAppA;

FIG. 3 shows the sequences of the mutagenic primers;

FIG. 4 shows the gene sequence and the amino acid sequence of the Ec-V90T mutant;

FIG. 5 shows the gene sequence and the amino acid sequence of the wild-type r-AppA;

FIG. 6 shows the gene sequence and the amino acid sequence of the r-N204A mutant;

FIG. 7 shows the gene sequence and the amino acid sequence of the r-S206A mutant;

DETAILED DESCRIPTION OF THE PREFERRED EMBODIMENT

Figure 1:
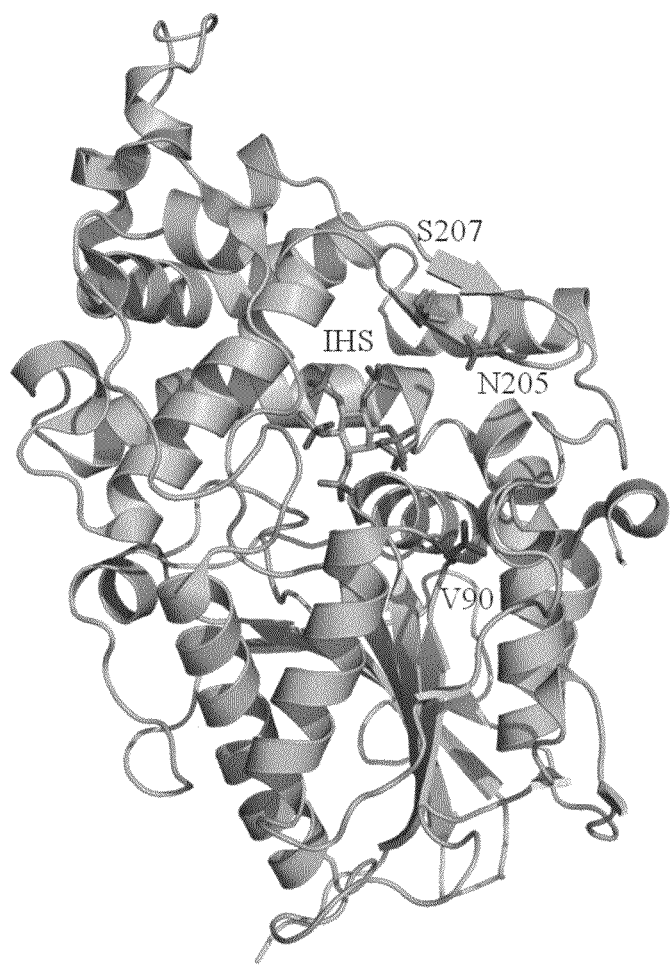
FIG. 1 shows the protein structure of the wild-type EcAppA and the amino acid residues to be modified.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

In the present invention, the gene of the phytase EcAppA was isolated from *Escherichia coli*, and EcAppA is a histidine acid phosphatase (HAP). EcAppA has high enzymatic activity, high substrate specificity and favorable pH profile for feed additive, and thus possesses high industrial value. In addition, large scale production of EcAppA in the industrial strain of *Pichia pastoris* has been successfully achieved and the structure of EcAppA has been solved. Therefore, EcAppA is a suitable target for enzyme modification to improve its enzymatic activity.

Since EcAppA originally has high enzymatic activity, it is difficult to find out mutations having much higher enzymatic activity by random mutagenesis. Even though the enzymatic activity is increased, it may not have significant difference to be distinguished from wild-type EcAppA, which results difficulty in screening. Therefore, the rational design is utilized in the present invention to narrow down the screening range by analyzing information of protein structure and sequence, so as to successfully find out the mutations having improved enzymatic activity.

The protein sequences of two novel HAPs, CaAppA (identified from *Citrobacter amalonaticus*) and CbAppA (identified from *Citrobacter braakii*), were compared with that of EcAppA. The result shows CaAppA and CbAppA both have 60% identity and 70% similarity with EcAppA, and CaAppA and CbAppA have 70% identity and 80% similarity with each other. By comparison of these three phytases which have high protein sequence similarity and high enzymatic activity, the mutations to be screened can be significantly reduced.

The amino acid residues which are identical in CaAppA and CbAppA but different in EcAppA were selected first. Then the positions of the residues were further analyzed, and only the residues located in the active site of EcAppA were further selected for site-directed mutagenesis, since the residues located in the active site have higher possibility in influencing the enzymatic activity of the enzyme. According to the above, Valine at position 90 was targeted for site-directed mutagenesis.

Moreover, when EcAppA is expressed in *Pichia pastoris*, the Asparagine residue, where the second following amino acid is Serine or Tyrosine but the first following amino acid thereof is not Proline, may be glycosylated. From sequence analysis, there are three putative Asparagine residues having potential to be glycosylated, but only one is located on the edge of the active site. Therefore, this Asparagine (located at position 205 in the original amino acid sequence) and the second following amino acid Serine (located at position 207 in the original amino acid sequence) were targeted for site-directed mutagenesis to produce de-glycosylated mutants.

FIG. 1 shows the protein structure of the wild-type EcAppA and the amino acid residues to be modified. EcAppA belongs to the HAP family, and the phytases in this family have similar structures, wherein the upper part is composed of α-helix and has a variable structure, and the lower part is composed of α-helix and β-sheet and has a more regular structure. IHS (inositol hexasulfate) is a compound using sulfate to replace the phosphorous in phytic acid, and is used to indicate the binding position of the phytic acid in phytase. The targeted amino acid residues V90, N205 and S207 for modification are also shown in FIG. 1.

The enzyme modification process of EcAppA, including site-directed mutagenesis, protein expression and activity assay, and the resulted phytase proteins are described in detail as follows.

First, the EcAppA gene sequence used in the present invention was *Escherichia coli* K12 AppA (GenBank NC_000913.2) without signal peptide, which is expressed from the 67th base and has few natural base mutations including T266C (from Valine to Alanine), A302T (from Glutamine to Leucine) and C835T (same amino acid). With the addition of start codon ATG, the sequence of EcAppA is shown in FIG. 2, wherein the full length of the EcAppA gene sequence is 1236 base pairs (SEQ ID NO: 1), which encodes a protein of 411 amino acids (SEQ ID NO: 2). The EcAppA gene was constructed into pET22b vector by using EcoRI and XhoI sites. The mutagenic primers of polymerase chain reaction (PCR) for site-directed mutagenesis are shown in FIG. 3, wherein Ec-V90T means Valine at position 90 was mutated into Threonine; in other words, the modification is a substitution of Valine at position 90 with Threonine. The sequence of the Ec-V90T mutant is shown in FIG. 4, wherein the gene sequence is numbered as SEQ ID NO: 3, and the amino acid sequence is numbered as SEQ ID NO: 4.

The original template was removed via DpnI digestion under 37° C., and then the plasmid with the mutated gene was transformed into *E. coli* XL1B competent cells. The transformants were cultured on LB plates containing 100 μg/ml Ampicillin at 37° C. for 1 day and screened with Ampicillin. The mutated gene was confirmed by DNA sequencing, and the plasmid with the mutated gene was further transformed into *E. coli* BL21 (DE3) for protein expression and purification.

The transformed strains were cultured in LB medium containing 100 μg/ml Ampicillin. First, the transformed strains were inoculated into 5 ml LB medium for 6 hours and then amplified into 200 ml LB medium, and finally amplified into 2 L LB medium. When OD600 reached 0.6-0.8, the protein expression was induced by adding 1 mM IPTG. Afterward, the cells were collected by centrifugation at 6000 rpm for 20 min. The cells were lysed in lysis buffer by sonicator and then centrifuged at 15000 rpm for 30 min to collect supernatants for purification. For obtaining highly purified protein, the Ec-V90T mutant protein was purified by FPLC system using DEAE column and had above 95% purity.

Phytase activity was measured as follows. First, 4 ml 7.5 mM sodium phytate, 0.2 ml enzyme protein (in buffer of 0.05% Triton X-100, 0.05% BSA and 0.25 M sodium acetate, pH5.5) and 1.8 ml 0.25 M sodium acetate (pH5.5) were incubated at 37° C. for 30 min. The reaction was stopped by adding 4 mL stop reagent (water:nitric acid:10% ammonium molybdate:0.2 M ammonium vanadate=4:2:1:1). OD450 was measured and then converted into enzyme activity unit. One unit of phytase activity is defined as the amount of enzyme required to liberate 1 μmol of inorganic phosphate from 5 mM sodium phytate per minute.

In *Pichia* expression system, the codon usage of EcAppA with reference to GenBank DQ513832.1 was optimized for *P. pastoris* expression. The optimized sequence r-AppA was expressed in *P. pastoris* as external secretion. A signal peptide was added in N-terminal of the sequence, and Methionine at position 1 was moved to the signal peptide. Since the signal peptide was removed during the process of protein expression, the secretary protein r-AppA had one less amino acid than the original sequence. The sequence of r-AppA is shown in FIG. 5, wherein the full length of the r-AppA gene sequence is 1233 base pairs (SEQ ID NO: 5), which encodes a protein of 410 amino acids (SEQ ID NO: 6). The r-AppA gene was constructed into pPICZαA vector by using EcoRI and NotI sites, and a natural mutation of A116V is resulted during construction. The mutagenic primers of polymerase chain reaction (PCR) for site-directed mutagenesis are shown in FIG. 3. The r-N204A mutant means Asparagine at position 204 was mutated into Alanine, that is to say, the modification is a substitution of Asparagine at position 204 with Alanine, and the sequence of r-N204A is shown in FIG. 6, wherein the gene sequence is numbered as SEQ ID NO: 7, and the amino acid sequence is numbered as SEQ ID NO: 8. The r-S206A mutant means Serine at position 206 was mutated into Alanine, that is to say, the modification is a substitution of Serine at position 206 with Alanine, and the sequence of r-S206A is shown in FIG. 7, wherein the gene sequence is numbered as SEQ ID NO: 9, and the amino acid sequence is numbered as SEQ ID NO: 10.

The plasmid DNA was linearized by PmeI and transformed into *P. pastoris* by electroporation. The transformants were selected on YPD plates containing 100 μg/mL Zeocin and incubated at 30° C. for 2 days. The picked colonies were inoculated into 5 ml YPD medium at 30° C. and further amplified into 50 ml BMGY medium at 30° C. overnight. After that, the cultured medium was changed to 20 ml BMMY with 0.5% methanol to induce the target protein expression. The samples were collected at different time points for every 24 hours, and meanwhile, the methanol was added into the flask to the final concentration of 0.5%. After induction for 4 days, the cells were harvested by centrifugation and the supernatant was collected for activity assay as described above.

To further amplify the production of phytase in industrial scale, the transformed cells were inoculated into 5 ml YPD medium at 30° C. overnight. Then, the culture was amplified into 2 L YPD medium and further transferred to 19 L fermentation medium (FBSM) in a 50 L fermentor. During fermentation process, temperature was maintained at 30° C. and pH was fixed to 5.0 by adding ammonium hydroxide. Dissolved oxygen was maintained above 40% by air flow rate and agitation rate. After batch phase, the carbon source was added by feeding 50% glycerol. Methanol was added to induce the protein expression. The cells were further harvested by centrifugation and the supernatant was collected for activity assay as described above.

Figure 8:
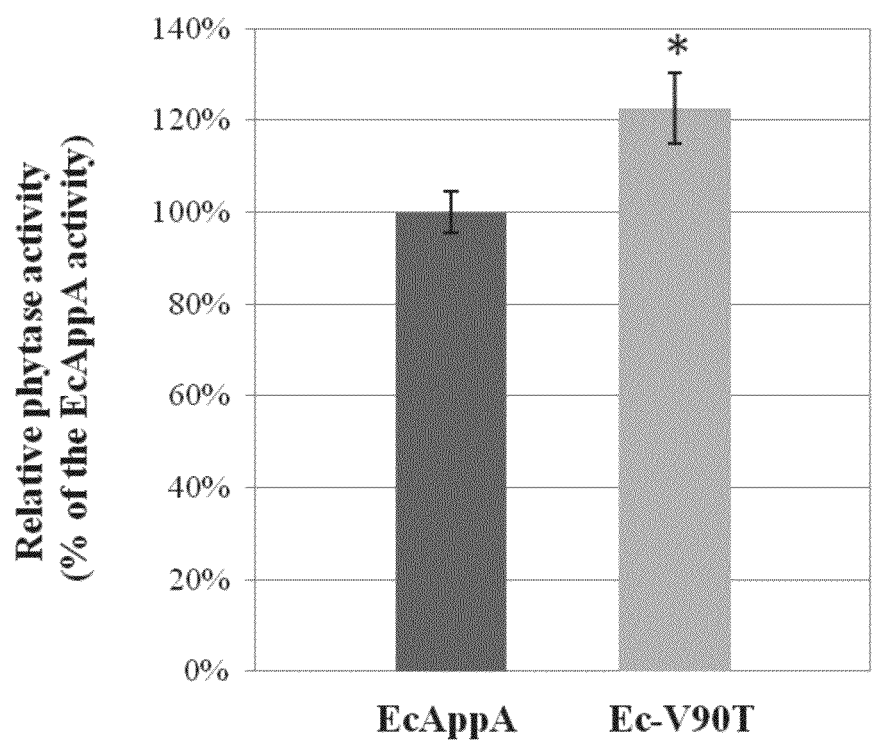
FIG. 8 shows the phytase activity analysis of the wild-type EcAppA and the Ec-V90T mutant.

FIG. 8 shows the phytase activity analysis of the wild-type EcAppA and the Ec-V90T mutant. The phytase activity of the wild-type EcAppA was set to 100%. The standard error of the mean (SEM) was also shown in the figure. Two-tailed P values were determined by an unpaired Student's t-test, and when P<0.05, it is determined there is a significant difference (*). The result indicated that the specific activity of enzyme was increased about 20% when Valine at position 90 was mutated into Threonine.

Figure 9:
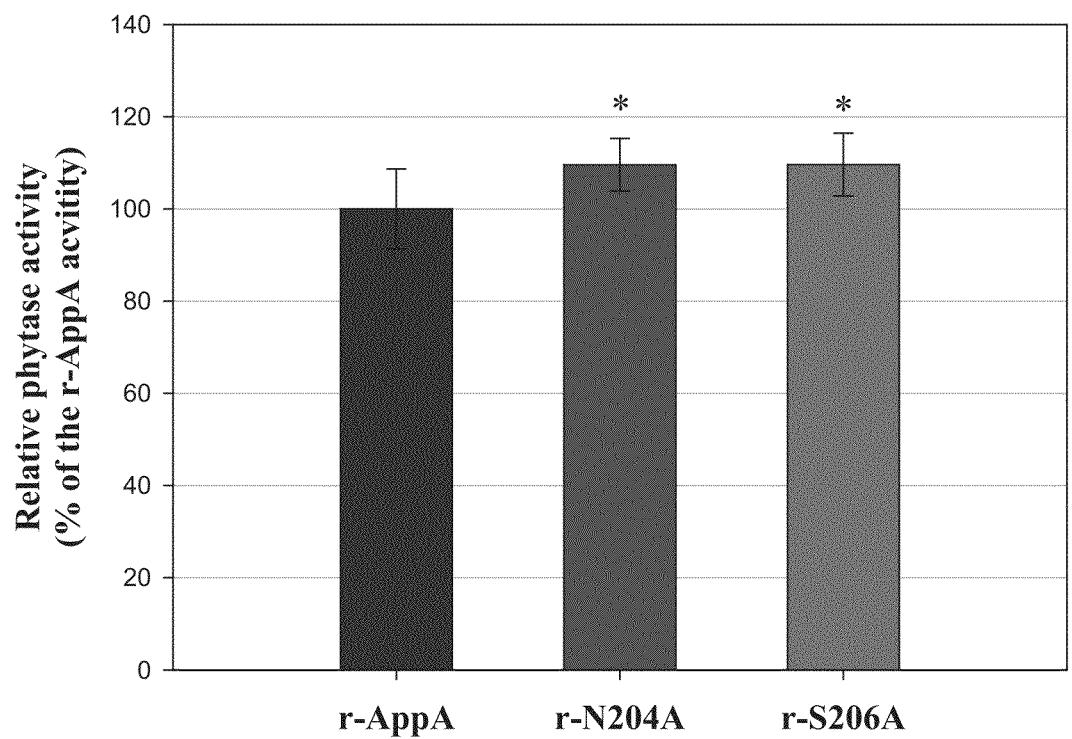
FIG. 9 shows the phytase activity analysis of the wild-type r-AppA and the r-N204A and r-S206A mutants.

FIG. 9 shows the phytase activity analysis of the wild-type r-AppA and the r-N204A and r-S206A mutants. The phytase activity of the wild-type r-AppA was set to 100%. The standard error of the mean (SEM) was also shown in the figure. Two-tailed P values were determined by an unpaired Student's t-test, and when P<0.05, it is determined there is a significant difference (*). The result indicated that the specific activities of the de-glycosylated mutants r-N204A and r-S206A were both increased about 10% when compared with the wild-type r-AppA.

From the above, in order to increase the industrial value of phytase, the present invention compared the sequences of EcAppA with other phytases having high enzymatic activity and analyzed the structure of EcAppA to select the amino acid residue located in the active site as the target for site-directed mutagenesis. It is observed that when Valine at position 90 was mutated into Threonine, the specific activity of the mutant Ec-V90T was increased about 20% when compared with the wild-type EcAppA. Further, in consideration of the glycosylation influence in *Pichia* expression system, the present invention designed mutants to remove the glycosylation position in the active site by site-directed mutagenesis. It is observed the specific activities of the de-glycosylated mutants r-N204A and r-S206A were both increased about 10% when compared with the wild-type r-AppA.

Since EcAppA originally has high enzymatic activity, it is difficult to find out mutations having much higher enzymatic activity, and even though the enzymatic activity is increased, it may not have significant difference. The mutant enzymes provided in the present invention increased the enzymatic activity about 1020%, but such increment was easy to be missed in large scale screening with random mutagenesis. However, the present invention utilized rational design to narrow down the screening range by analyzing information of protein structure and sequence, so as to successfully find out the mutations having improved enzymatic activity. Since phytase is estimated to account for 60% of feed enzyme products, once the enzymatic activity of phytase is improved, the production cost will be reduced and the profit will be increased. Therefore, the present invention successfully modified EcAppA to improve the enzymatic activity thereof, and thus, the present invention possesses high industrial value.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A phytase comprising a modified amino acid sequence of SEQ ID NO: 2, wherein the modification is a substitution of Valine at position 90 with Threonine.

2. The phytase according to claim 1 wherein the amino acid sequence of SEQ ID NO: 2 is encoded by EcAppA gene isolated from *Escherichia coli*.

3. The phytase according to claim 1 being a histidine acid phosphatase.

4. The phytase according to claim 1 having a full length amino acid sequence of SEQ ID NO: 4.

5. A phytase comprising a modified amino acid sequence of SEQ ID NO: 6, wherein the modification is a substitution of Asparagine at position 204 with Alanine or a substitution of Serine at position 206 with Alanine to remove a glycosylation position in an active site of the phytase.

6. The phytase according to claim 5 wherein the amino acid sequence of SEQ ID NO: 6 is encoded by EcAppA gene isolated from *Escherichia coli* and optimized with codon usage.

7. The phytase according to claim 5 being a histidine acid phosphatase.

8. The phytase according to claim 5 having a full length amino acid sequence of SEQ ID NO: 8.

9. The phytase according to claim 5 having a full length amino acid sequence of SEQ ID NO: 10.

* * * * *